(12) United States Patent
Keimel et al.

(10) Patent No.: US 8,135,470 B2
(45) Date of Patent: Mar. 13, 2012

(54) ENERGY BALANCE THERAPY FOR OBESITY MANAGEMENT

(75) Inventors: John G. Keimel, North Oaks, MN (US); Warren L. Starkebaum, Plymouth, MN (US); Gary L. Lubben, Independence, MN (US)

(73) Assignee: Medtronic, Inc., Minneapolis, MN (US)

( * ) Notice: Subject to any disclaimer, the term of this patent is extended or adjusted under 35 U.S.C. 154(b) by 212 days.

(21) Appl. No.: 12/476,893

(22) Filed: Jun. 2, 2009

(65) Prior Publication Data
US 2009/0240194 A1  Sep. 24, 2009

Related U.S. Application Data

(62) Division of application No. 11/414,500, filed on Apr. 28, 2006, now Pat. No. 7,558,629.

(51) Int. Cl.
*A61N 1/36* (2006.01)
(52) U.S. Cl. .......................... 607/40; 607/133
(58) Field of Classification Search .................. 607/40
See application file for complete search history.

(56) References Cited

U.S. PATENT DOCUMENTS

| | | | |
|---|---|---|---|
| 4,823,808 A | 4/1989 | Clegg et al. | |
| 5,188,104 A * | 2/1993 | Wernicke et al. | 607/40 |
| 5,417,713 A | 5/1995 | Cohen | |
| 6,044,297 A | 3/2000 | Sheldon et al. | |
| 6,120,467 A | 9/2000 | Schallhorn | |
| 6,611,715 B1 * | 8/2003 | Boveja | 607/40 |
| 6,659,968 B1 | 12/2003 | McClure | |
| 6,735,479 B2 | 5/2004 | Fabian et al. | |
| 6,810,349 B2 | 10/2004 | Westerterp et al. | |
| 6,975,904 B1 | 12/2005 | Sloman | |
| 7,162,304 B1 | 1/2007 | Bradley | |
| 7,415,308 B2 | 8/2008 | Gerber et al. | |
| 7,558,629 B2 | 7/2009 | Keimel et al. | |
| 2002/0082658 A1 | 6/2002 | Heinrich et al. | |
| 2003/0144708 A1 | 7/2003 | Starkebaum | |
| 2004/0133081 A1 | 7/2004 | Teller et al. | |
| 2004/0147816 A1 | 7/2004 | Policker et al. | |

(Continued)

FOREIGN PATENT DOCUMENTS

WO   WO 2006/126918 A1   11/2006

OTHER PUBLICATIONS

U.S. Appl. No. 11/414,732, filed Apr. 28, 2006, entitled "Activity Level Feedback for Managing Obesity", Lu et al.

(Continued)

*Primary Examiner* — Carl H Layno
*Assistant Examiner* — Luther Behringer
(74) *Attorney, Agent, or Firm* — Jeffrey J. Hohenshell

(57) ABSTRACT

Techniques are described that allow an implantable device to sense gastric data and activity data from a patient, and estimate the patient's amount of energy consumed and energy expended based on the sensed data. A system provides feedback to the patient, a family member, or a doctor about the patient's energy consumed, energy expended, and net energy. The data may be provided in table or graphical format, and may show daily or weekly energy balance data or may show a trend of the daily or weekly energy data. The patient may receive feedback by an implanted alert module that provides and audio alert or a vibration alert. In addition, data acquired by the system may be used to adjust the patient's stimulation therapy parameters.

35 Claims, 8 Drawing Sheets

U.S. PATENT DOCUMENTS

| | | | |
|---|---|---|---|
| 2004/0236382 A1* | 11/2004 | Dinsmoor et al. | 607/40 |
| 2005/0090873 A1* | 4/2005 | Imran | 607/40 |
| 2005/0113650 A1 | 5/2005 | Pacione et al. | |
| 2005/0149142 A1 | 7/2005 | Starkebaum | |
| 2005/0245986 A1 | 11/2005 | Starkebaum | |
| 2006/0074459 A1 | 4/2006 | Flesler et al. | |
| 2006/0136004 A1* | 6/2006 | Cowan et al. | 607/33 |
| 2007/0118056 A1 | 5/2007 | Wang et al. | |
| 2007/0129641 A1 | 6/2007 | Sweeney | |

OTHER PUBLICATIONS

Bouten et al., "A Triaxial Accelerometer and Portable Data Processing Unit for the Assessment of Daily Physical Activity," IEEE Transactions on Biomedical Engineering, vol. 44, No. 3, Mar. 1997, pp. 136-147.

Office Action dated Aug. 6, 2009 for U.S. Appl. No. 11/414,732 (10 pgs.).

Responsive Amendment dated Nov. 4, 2009 for U.S. Appl. No. 11/414,732 (20 pgs.).

Office Action dated Mar. 16, 2010 for U.S. Appl. No. 11/414,732 (12 pgs.).

Responsive Amendment dated May 14, 2010 for U.S. Appl. No. 11/414,732 (24 pgs.).

Advisory Action dated Jun. 4, 2010 for U.S. Appl. No. 11/414,732 (7 pgs.).

Request for Continued Examination and Responsive Amendment dated Jun. 16, 2010 for U.S. Appl. No. 11/414,732 (19 pgs.).

\* cited by examiner

ENERGY BALANCE THERAPY FOR OBESITY MANAGEMENT

This application is a Divisional of U.S. application Ser. No. 11/414,500, filed Apr. 28, 2006, now U.S. Pat. No. 7,558,629 on Jul. 7, 2009, the entire content of which is incorporated herein by reference.

TECHNICAL FIELD

The invention relates to implantable medical devices and, more particularly, implantable medical devices for obesity management.

BACKGROUND

Obesity is a serious health problem for many people. Patients who are overweight often have problems with mobility, sleep, high blood pressure, and high cholesterol. Some other serious risks also include diabetes, cardiac arrest, stroke, kidney failure, and mortality. In addition, an obese patient may experience psychological problems associated with health concerns, social anxiety, and generally poor quality of life.

Certain diseases or conditions can contribute to additional weight gain in the form of fat, or adipose tissue. However, healthy people may also become overweight as a net result of excess energy consumption and insufficient energy expenditure. Reversal of obesity is possible but difficult. Once the patient expends more energy than is consumed, the body will begin to use the energy stored in the adipose tissue. This process will slowly remove the excess fat from the patient and lead to better health. Some patients require intervention to help them overcome their obesity. In these severe cases, nutritional supplements, prescription drugs, or intense diet and exercise programs may not be effective.

Surgical intervention is a last resort treatment for some obese patients who are considered morbidly obese. One common surgical technique is the Roux-en-Y gastric bypass surgery. In this technique, the surgeon staples or sutures off a large section of the stomach to leave a small pouch that holds food. Next, the surgeon severs the small intestine at approximately mid length and attaches the distal section of the small intestine to the pouch portion of the stomach. This procedure limits the amount of food the patient can ingest to a few ounces, and limits the amount of time that ingested food may be absorbed through the shorter length of the small intestine. While this surgical technique may be very effective, it poses significant risks of unwanted side effects, malnutrition, and death.

SUMMARY

In general, the invention is directed to techniques for energy balance therapy for obesity management. Energy balance therapy may include providing feedback to a patient regarding amounts of energy that the patient has consumed and expended, and the difference between these amounts, i.e., the patient's net energy. Additionally, or alternatively, energy balance therapy may include modifying electrical stimulation parameters to control gastric therapy based on amounts of energy consumed and expended. Obesity is an increasing problem for many people, as individuals are consuming more calories and exercising less frequently than necessary to maintain body weight.

In some cases, traditional methods for reducing body weight in obese patients may be ineffective, impractical, or potentially dangerous. For a patient to lose weight, the patient must have a net energy such that energy expended is greater than energy consumed. The techniques of the invention allow an implantable device to sense gastric data and activity data from the patient, and estimate the patient's amount of energy consumed and energy expended based on the sensed data.

A system may provide feedback to the patient, a family member, or a physician about the patient's energy consumed, energy expended, and net energy. The data may be provided in table or graphical format, and may show daily or weekly energy balance data or may show a trend of the daily or weekly energy data. The patient may receive feedback from an implanted alert module that provides an audio alert or a vibration alert. Alternatively, or additionally, the patient may receive feedback via an external device that receives data via wireless telemetry from an implanted device.

In addition, the energy balance data acquired by the system may be used to modify stimulation therapy parameters associated with electrical stimulation delivered to the patient by an implantable gastric stimulator. In some embodiments, some or all of the components of the sensing device may be integrated with an implantable gastric stimulator. In other embodiments, the sensing device may communicate data to the implantable gastric stimulator either directly or via an external device using wireless telemetry.

In one embodiment, the disclosure provides a method comprising receiving gastric data sensed by an implantable device implanted within a patient, estimating an amount of energy consumed by the patient based on the sensed gastric data, and controlling therapy to the patient based on the amount of energy consumed. Controlling therapy may include, for example, providing feedback based on the amount of energy consumed, modifying electrical stimulation parameters of an implantable stimulator implanted within the patient based on the estimated amount of energy consumed, or both.

In another embodiment, the disclosure provides a method comprising receiving activity data sensed by an implantable device implanted within a patient, estimating an amount of energy expended by the patient based on the sensed activity data, and modifying electrical stimulation parameters of an implantable stimulator implanted within the patient based on the estimated amount of energy expended.

In an additional embodiment, the disclosure provides a method comprising receiving an estimated amount of energy expended by a patient, receiving an estimated amount of energy consumed by the patient, wherein at least one of the estimated amount of energy expended and the estimated amount of energy consumed is estimated based on sensed data received from an implantable device implanted within the patient, and calculating an amount of net energy based on the amounts of energy expended and energy consumed.

In another embodiment, the disclosure provides an implantable device comprising a sensor to sense gastric data, and a processor to estimate an amount of energy consumed by a patient based on the sensed gastric data and control therapy to the patient based on the amount of energy consumed.

In a further embodiment, the disclosure provides a system comprising an implantable device that senses gastric data and estimates an amount of energy consumed by a patient based on the sensed gastric data, and an external module, wherein the implantable device transmits a wireless communication to the external module to provide feedback based on the amount of energy consumed.

In other embodiments, the disclosure contemplates computer-readable media comprising instructions that cause a programmable processor to receive gastric data sensed by an implantable device implanted within a patient, estimate an amount of energy consumed by the patient based on the sensed gastric data, and provide feedback based on the amount of energy consumed.

In various embodiments, the invention may provide one or more advantages. For example, the energy feedback to the patient may be combined with delivery of electrical stimulation to the stomach to cause a sensation of fullness or nausea that prevents a patient from ingesting excessive amounts of food, or small intestine stimulation to promote motility and decreased caloric absorption. This technique for treating obesity may provide an opportunity for some patients to lose dangerous excess fat without the potential dangers associated with current surgical techniques. Moreover, biofeedback conditioning of the patient could lead to reduced dependency on the stimulation, modification of the therapy, and eventual discontinuation of treatment.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
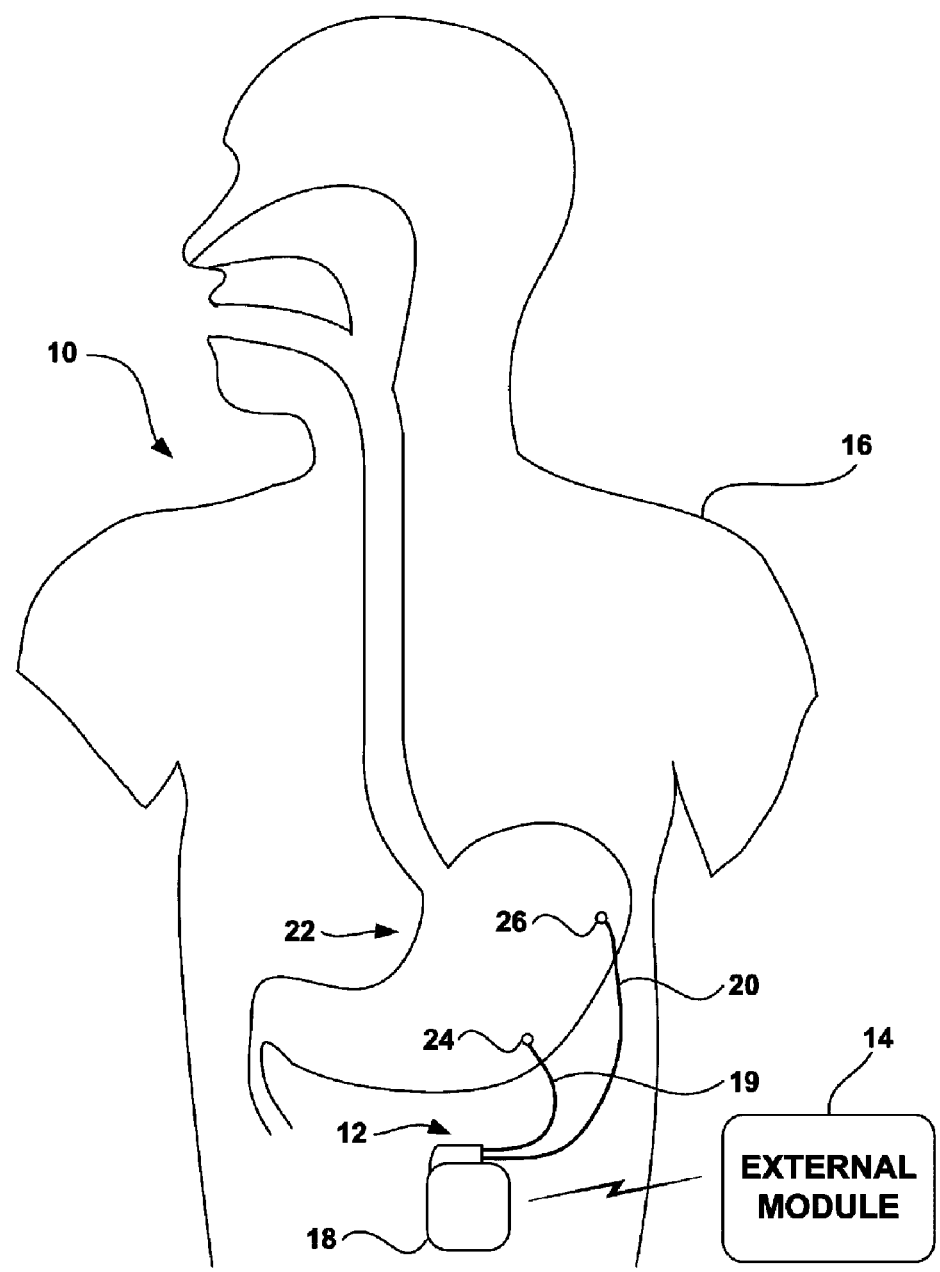
FIG. 1 is a schematic diagram illustrating an implantable stimulation system.

FIG. 1 is a schematic diagram illustrating an implantable stimulation system 10. System 10 is configured to provide energy balance feedback for treatment of obesity. For example, system 10 may provide feedback to patient 16 regarding energy consumption and energy expenditure by patient 16. System 10 may also be configured to deliver gastric stimulation therapy for treatment of obesity, and may control stimulation parameters as a function of energy balance. In general, system 10 is designed to help the patient balance food intake and exercise in favor of weight loss by providing feedback. The energy intake information may be obtained by sensing consumption of food. The energy expenditure information may be obtained by sensing physical activity. In some embodiments, system 10 may support the presentation of long term trends in food consumption and exercise to aid the patient in losing weight.

As shown in FIG. 1, system 10 may include an implantable stimulator 12 and external module 14 shown in conjunction with patient 16. Stimulator 12 includes a pulse generator 18 that generates electrical stimulation pulses. One or more leads 19, 20 carry the electrical stimulation pulses to stomach 22.

Leads 19, 20 each include one or more electrodes 24, 26 for delivery of the electrical stimulation pulses to stomach 22. Although the electrical stimulation pulses may be delivered to other areas within the gastrointestinal tract, such as the esophagus, duodenum, small intestine, or large intestine, delivery of stimulation pulses to stomach 22 will generally be described in this disclosure for purposes of illustration. In some embodiments, system 10 may include a drug delivery device that delivers drugs or other agents to the patient for obesity therapy.

For patient 16 to lose weight, patient 16 must have a net energy such that energy expended is greater than energy consumed. The term "net energy" refers to energy consumed minus energy expended. However, patient 16 may not have an accurate awareness of how much energy patient 16 is consuming or expending. Stimulator 12 may be configured to obtain information for calculating an amount of energy expended or consumed based on a variety of sensed physiological parameters. In addition, stimulator 12 may deliver stimulation pulses to the gastrointestinal tract to limit food intake or caloric absorption, i.e., energy consumed.

System 10 may present feedback regarding energy consumed, energy expended, or net energy over a time period to patient 16. Patient 16 may modify his or her behavior in response to the feedback. In this manner, system 10 may provide a two-pronged therapy for obesity that includes both stimulation and energy balance feedback. System 10 may present energy balance data such as energy consumed, energy expended, or net energy to patient 16 or a family member or health care provider. The data may be provided in table or graphical format, and may show daily or weekly energy balance data or may show a trend of the daily or weekly energy data. In addition, the energy balance data acquired by system 10 may be used to adjust stimulation therapy. If energy intake outpaces energy expenditure, for example, system 10 may adjust stimulation therapy to discourage food intake or reduce caloric absorption.

At the surface lining of stomach 22, leads 19, 20 penetrate into tissue such that electrodes 24 and 26 are positioned to deliver stimulation to the stomach. The stimulation pulses generated by stimulator 12 may be applied to induce nausea or satiety in response to monitored parameters. For example, the stimulation pulses may slow or retard the emptying of stomach 22 to provide extended periods of satiety. The induced sensation of satiety or nausea may reduce a patient's desire to consume large portions of food. Alternatively, the stimulation pulses may cause the smooth muscle of stomach 22 to contract and slowly move contents from the entrance toward the exit of the stomach. Alternatively, or additionally, the electrical stimulation pulses may stimulate nerves within stomach 22 to cause muscle contraction and thereby restore or enhance gastrointestinal motility. Enhanced motility may serve to speed food through the gastrointestinal tract and reduce caloric absorption. Again, the stimulation pulses may be delivered elsewhere within the gastrointestinal tract, either as an alternative to stimulation of stomach 22 or in conjunction with stimulation of the stomach.

Implantable stimulator 12 may be constructed with a biocompatible housing, such as titanium, stainless steel, or a polymeric material, and is surgically implanted within patient 16. The implantation site may be a subcutaneous location in the side of the lower abdomen or the side of the lower back. Pulse generator 18 is housed within the biocompatible housing, and includes components suitable for generation of electrical stimulation pulses. Electrical leads 19 and 20 are flexible, electrically insulated from body tissues, and terminated with electrodes 24 and 26 at the distal ends of the respective leads. The leads may be surgically or percutaneously tunneled to stimulation sites on stomach 22. The proximal ends of leads 19 and 20 are electrically coupled to pulse generator 18 via internal conductors to conduct the stimulation pulses to stomach 22 via electrodes 24, 26. For embodiments in which system 10 includes a drug delivery device, the drug delivery device may include one or more implantable pumps and one or more implantable catheters for delivery of a drug to the patient, as well as a controller for the pump. The controller may be responsive to an external programmer or other control signals or feedback to adjust dosage and rate. The energy balance data acquired by the system may be used to modify dosing parameters associated with the drug delivery device. For example, the dosing parameters may be automatically adjusted, or a recommended dosage change may be sent.

Leads 19, 20 may be placed into the muscle layer or layers of stomach 22 via an open surgical procedure, or by laparoscopic surgery. Leads also may be placed in the mucosa or submucosa by endoscopic techniques, or by an open surgical procedure or laparoscopic surgery. Electrodes 24, 26 may form a bipolar pair of electrodes. Alternatively, pulse generator 18 may carry a reference electrode to form an "active can" arrangement, in which one or both of electrodes 24, 26 are unipolar electrodes referenced to the electrode on the pulse generator. The housing of implantable stimulator 12 may itself serve as a reference electrode. A variety of polarities and electrode arrangements may be used.

In addition to pulse rate, the stimulation pulses delivered by implantable stimulator 12 are characterized by other stimulation parameters such as a voltage or current amplitude and pulse width. The stimulation parameters may be fixed, adjusted in response to sensed physiological conditions within or near stomach 22, or adjusted in response to patient input entered via external module 14. For example, in some embodiments, patient 16 may be permitted to adjust stimulation amplitude and turn stimulation on and off.

As an illustration, the stimulation pulses delivered by stimulator 12 may have a pulse amplitude in a range of approximately 1 to 10 volts, a pulse width in a range of approximately 50 microseconds to 10 milliseconds, and a pulse rate in a range of approximately 1 to 100 Hz. The pulse rate is more preferably in a range of approximately 2 to 40 Hz, and even more preferably in a range of approximately 5 to 20 Hz. The terms pulse rate and pulse frequency may be used interchangeably in this description. In some embodiments, an instant start to delivery of the stimulation pulses may be provided. However, a gradual ramp up in stimulation intensity may be applied to prevent muscle shock and patient discomfort. This ramp may be in the form of a gradually increasing pulse rate, amplitude, or pulse width.

One or both of leads 19, 20 may carry a sense electrode, in addition to stimulation electrodes 24, 26, to sense physiological parameters that may be used to estimate an amount of energy consumed or expended by patient 16. Alternatively, an additional lead or device may be provided and dedicated to sensing of physiological parameters. Sensing may occur continuously, periodically, or intermittently, as therapy dictates. For example, some sensing may take place at predetermined times of the day, e.g., at meal times, or continuously over the course of the day to ensure that substantially all food intake and physical activity information is obtained. Information relating to the sensed data may be stored in memory within pulse generator 18 for retrieval and analysis at a later time. Alternatively, the sensed data may be immediately transmitted to external module 14 by wired or wireless telemetry.

Stimulator 12 also may include telemetry electronics to communicate with external module 14. External module 14 may be a small, battery-powered, portable device that accompanies patient 16 throughout a daily routine. External module 14 may have a simple user interface, such as a button or keypad, and a display or lights. External module 14 may be a hand-held device configured to permit activation of stimulation and adjustment of stimulation parameters. Alternatively, external module 14 may form part of a larger device including a more complete set of programming features including complete parameter modifications, firmware upgrades, data recovery, or battery recharging in the event stimulator 12 includes a rechargeable battery. External module 14 may be a patient programmer, a physician programmer, or a patient monitor. In some embodiments, external module 14 may be a general purpose device such as a cellular telephone, a wristwatch, a personal digital assistant (PDA), or a pager.

In some example embodiments, implantable stimulator 12 may communicate sensed physiological parameters to external module 14. The communication may occur wirelessly, or in the case of a percutaneous lead implantable stimulator 12 may have a wired connection. However, in most cases in which implantable stimulator 12 is fully implanted, communication between implantable stimulator 12 and external module 14 will occur wirelessly. Communication may occur continuously, periodically, or intermittently. External module 14 may analyze the sensed parameters to obtain values for energy consumed, energy expended, and net energy. Alternatively, external module 14 may transmit the received sensed parameters to another device for analysis, such as a central server accessed by external module 14 via the Internet. In other embodiments, implantable stimulator 12 may include a processor that performs analysis of the sensed parameters, and communicates estimated energy consumed, energy expended, or other energy balance data to external module 14. Accordingly, the computing resources for analysis of energy balance may be provided within stimulator 12, external module 14 or elsewhere.

External module 14 may present feedback to patient 16 regarding energy consumed, energy expended, and/or net energy. Alternatively, such feedback may be presented by a central server via a webpage to patient 16, or a caregiver, family member, or health service provider of patient 16. Stimulator 12 may provide an alert to patient 16 to indicate, for example, to stop eating, or to increase activity level. Stimulator 12 may adjust stimulation therapy in response to the net energy or other energy balance data. For example, stimulator 12 may increase or decrease the level or duration of stimulation.

In some embodiments, system 10 may include multiple implantable stimulators 12 to stimulate a variety of regions of stomach 22. Stimulation delivered by the multiple stimulators may be coordinated in a synchronized manner, or performed without communication between stimulators. Also, the electrodes may be located in a variety of sites on the stomach, or elsewhere in the gastrointestinal tract, dependent on the particular therapy or the condition of patient 12.

In some embodiments, electrodes on implantable stimulator 12 or attached to implantable stimulator 12 with a lead extension may measure an amount of local adipose tissue on patient 16, e.g., through electrical impedance measurements. This information may be used in conjunction with patient weight information to calculate a value correlated to percent body fat. This information could be used to aid in feedback to patient 16 or other users, for example in trend charts.

The electrodes carried at the distal end of each lead 19, 20 may be attached to the wall of stomach 22 in a variety of ways. For example, the electrode may be surgically sutured onto the outer wall of stomach 22 or fixed by penetration of anchoring devices, such as hooks, barbs or helical structures, within the tissue of stomach 22. Also, surgical adhesives may be used to attach the electrodes. In any event, each electrode is implanted in acceptable electrical contact with the smooth muscle cells within the wall of stomach 22. In some cases, the electrodes may be placed on the serosal surface of stomach 22, within the muscle wall of the stomach, or within the mucosal or submucosal region of the stomach.

Figure 2:
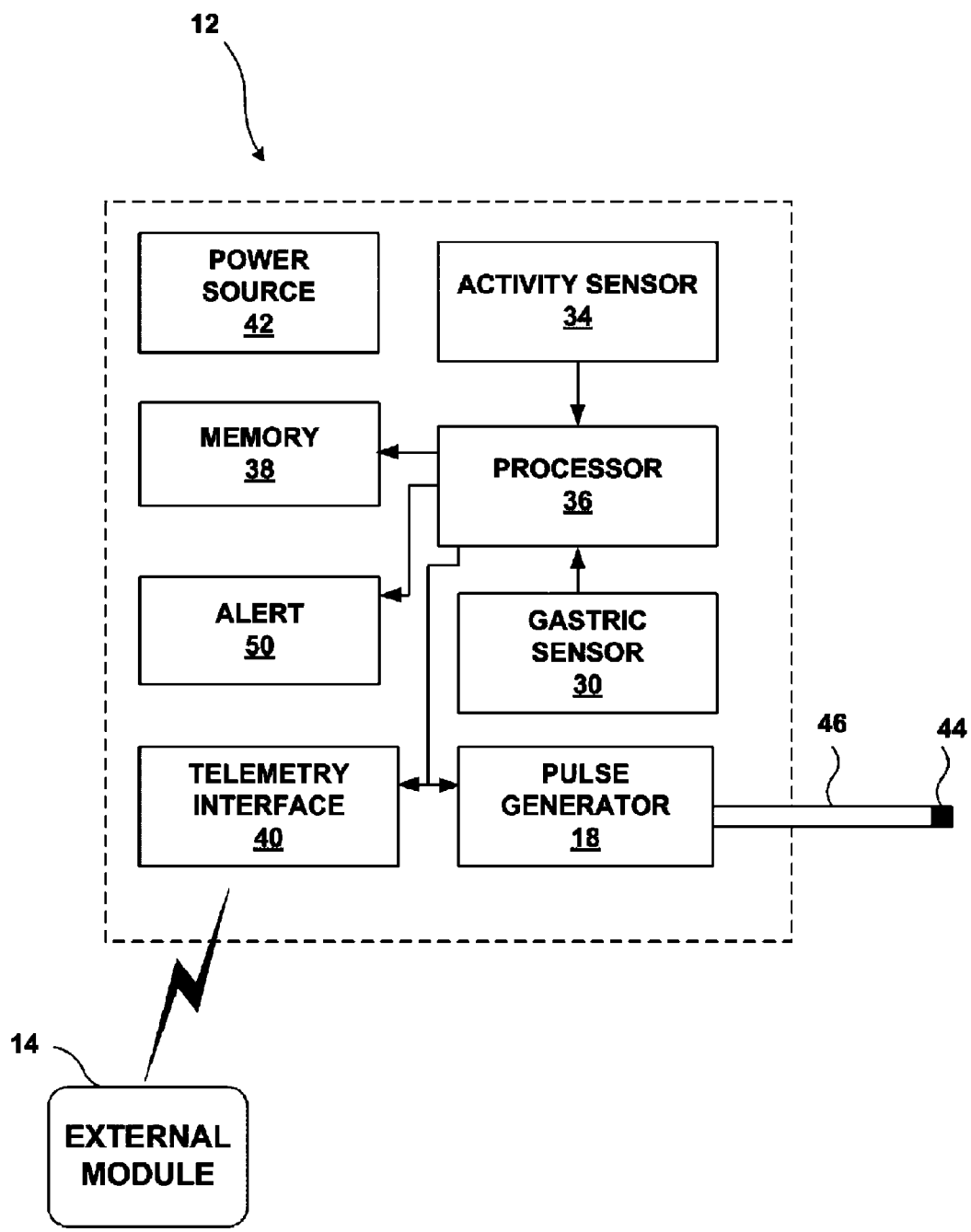
FIG. 2 is a block diagram illustrating an implantable stimulator in greater detail in accordance with an embodiment of the invention.

FIG. 2 is a block diagram illustrating implantable stimulator 12 in greater detail in accordance with an embodiment of the invention. In FIG. 2, implantable stimulator 12 includes gastric sensor 30. Signals detected by gastric sensor 30 may be representative of physiological parameters relating to gastric activity, such as food intake. For example, gastric sensor 30 may detect gastric contractions by sensing gastric electrical activity (e.g., gastric slow wave), by using a pressure sensor, by using a piezoelectric or triboelectric sensor, by using a strain gauge sensor, by using a gastric impedance sensor, or by using acoustic or ultrasonic sensors. Gastric sensor 30 supplies sensed gastric data to a processor 36.

Implantable stimulator 12 also includes an activity sensor 34. Activity sensor 34 detects signals used to estimate energy expenditure, such as signals representing heart rate, heart rate variability, electrocardiogram (ECG), Q-T interval, night heart rate, cardiac variability index, minute volume, minute ventilation, blood oxygen level, blood pressure, body temperature, or activity. Activity may be sensed by an accelerometer, which may be disposed within the housing of implantable stimulator 12, mounted on the header of stimulator 12, or coupled to implantable stimulator 12 via a lead. An accelerometer measures an activity level by measuring the acceleration of patient 16. An accelerometer used by implantable stimulator 12 may be a single axis accelerometer or a tri-axial accelerometer that uses piezoelectric materials. An accelerometer and circuitry that is able to provide a constant (DC) output may also be able to sense the orientation of patient 16, such as whether the patient is standing or lying down. This information may also be used in calculating energy expended. Activity sensor 34 supplies sensed activity data to processor 36.

Although shown for exemplary purposes with a single gastric sensor 30 and a single activity sensor 34, a plurality of sensors for each type of data may be coupled to implantable stimulator 12. One or more sensor amplifiers (not shown) receive signals detected by gastric sensor 30 and activity sensor 34. The sensor amplifier amplifies and filters the received signals and supplies the signals to processor 36.

Processor 36 processes the received signals, and may analyze a physiological parameter of interest. For example, processor 36 may estimate an amount of energy consumed based on the sensed gastric data, or an amount of energy expended based on the sensed activity data. Processor 36 may also calculate a net energy value by comparing the energy expended to the energy consumed. The received signal is typically converted to digital values prior to processing by processor 36, and stored in memory 38.

Memory 38 may include any form of volatile memory, non-volatile memory, or both. In addition to data sensed via gastric sensor 30 and activity sensor 34, memory 38 may store records concerning measurements of sensed gastric or activity data, communications to patient 16 or other information pertaining to operation of implantable stimulator 12. Memory 38 may also store information about patient 16, goal values for energy consumed, energy expended, and net energy, and thresholds for comparison to the sensed gastric and activity data. In addition, processor 36 is typically programmable, and programmed instructions reside in memory 38.

Wireless telemetry in stimulator 12 may be accomplished by radio frequency (RF) communication or proximal inductive interaction of implantable stimulator 12 with external module 14 via telemetry interface 40. Processor 36 controls telemetry interface 40 to exchange information with external module 14. Processor 36 may transmit operational information and sensed information to external module 14 via telemetry interface 40. For example, processor 36 may transmit sensed gastric and activity data, or other information relating to energy consumed and energy expended. In some embodiments, only activity data may be used to provide feedback. Also, in some embodiments, pulse generator 18 may communicate with other implanted devices, such as stimulators or sensors, via telemetry interface 40.

Power source 42 delivers operating power to the components of implantable stimulator 12. Power source 42 may include a battery and a power generation circuit to produce the operating power. In some embodiments, the battery may be rechargeable to allow extended operation. Recharging may be accomplished through proximal inductive interaction between an external charger and an inductive charging coil within implantable stimulator 12. In other embodiments, an external inductive power supply may transcutaneously power implantable stimulator 12 whenever stimulation therapy is to occur.

Implantable stimulator 12 is coupled to an electrode 44 by a lead 46. Implantable stimulator 12 provides stimulation therapy to the gastrointestinal tract of patient 16. Pulse generator 18 includes suitable pulse generation circuitry for generating a voltage or current waveform with a selected amplitude, pulse width, and frequency. In some embodiments, processor 36 may determine whether to direct application of electrical stimulation to patient 16 and/or adjust stimulation parameters based upon estimated energy balance data, e.g., values of energy consumed. Alternatively, or additionally, processor 36 may be responsive to instructions from external module 14 to direct application of electrical stimulation and/or adjust stimulation parameters.

Processor 36 may compare the estimated value of energy consumed to a goal value of energy consumed, and control a pulse generator 18 to apply an electrical stimulation signal via stimulation electrode 44 when the goal value for energy consumed is surpassed. In response to a control signal from processor 36, the electrical stimulation signal generated by pulse generator 18 may be applied to a patient's gastrointestinal tract. This electrical stimulation signal may be generated until processor 36 detects a cessation of gastric activity using sensed gastric data detected by gastric sensor 30, at which time processor 36 controls pulse generator 18 to stop delivery of the electrical stimulation.

Processor 36 may also record the occurrence of electrical stimulation within memory 38 for use in determining whether additional electrical stimulation is desired to increase an amount of negative biofeedback provided to the patient 16. For example, processor 36 stores an occurrence of electrical stimulation in memory 38. The next time processor 36 determines electrical stimulation is needed, processor 36 may search memory 38 to determine when the prior electrical stimulation occurred in order to estimate whether electrical stimulation for an extended period of time may be useful.

If a patient 16 consumes food on more occasions or for longer durations than may be specified in a particular treatment plan for obesity, electrical stimulation for extended periods of time beyond a baseline time period may be useful to encourage patients to reduce the duration or number of occasions in which food is consumed. Similarly, a record of the prior occurrence of electrical stimulation may be used to ensure that a minimum amount of time passes between the detection of gastric activity. When gastric activity is detected before the minimum amount of time has passed, electrical stimulation may also be provided for an extended period of time to discourage patient 16 from eating food as often.

In embodiments where processor 36 estimates energy consumed, energy expended, or net energy, processor 36 may communicate this energy balance information to patient 16 in a number of ways. Implantable stimulator 16 may wirelessly transmit the information to external module 14 using telemetry interface 40. External module 14 may notify patient 16 when energy consumed, energy expended, or net energy does not meet desired goal values. External module 14 may notify patient 16 in the form of a visible or audible notification, e.g., emitted by a light, LED, display, or audio speaker. A visible notification may be presented as text, graphics, one or more blinking lights, illumination of one or more lights, or the like. An audible notification may take the form of an audible beep, ring, speech message, vibration, or the like. In addition to transmitting a communication to an external module 14, telemetry interface 40 may be configured to wirelessly transmit information about the history or status of implantable stimulator 12 to a physician for patient 16.

In addition, or in the alternative, implantable stimulator 12 may include an alert module 50 that is implanted in the body of patient 16. When activated by processor 36, alert module 50 can notify patient 16 directly without use of external module 14. Alert module 50 may, for example, notify patient 16 audibly or by vibration. For example, alert module 50 may take the form of a piezoelectric transducer that is energized in response to a signal from processor 36 in order to emit a sound or vibration. Alternatively, alert module 50 may apply electrical stimulation to the patient 16 at a level or in a pattern that is noticeable. In each case, patient 16 may receive a communication that implantable stimulator 12 has detected an energy balance value not in accordance with a goal energy value. The communication may mean that patient 16 must take steps to adjust the energy balance. For example, a communication may indicate to patient 16 to stop eating or increase activity level. The patient alert may be used to discourage patient 16 from eating too much or too often. The timing and duration of alerts can be programmable. Also, when alert module 50 has been activated, the patient 16 may turn off the alert using external device 14.

Figure 3:
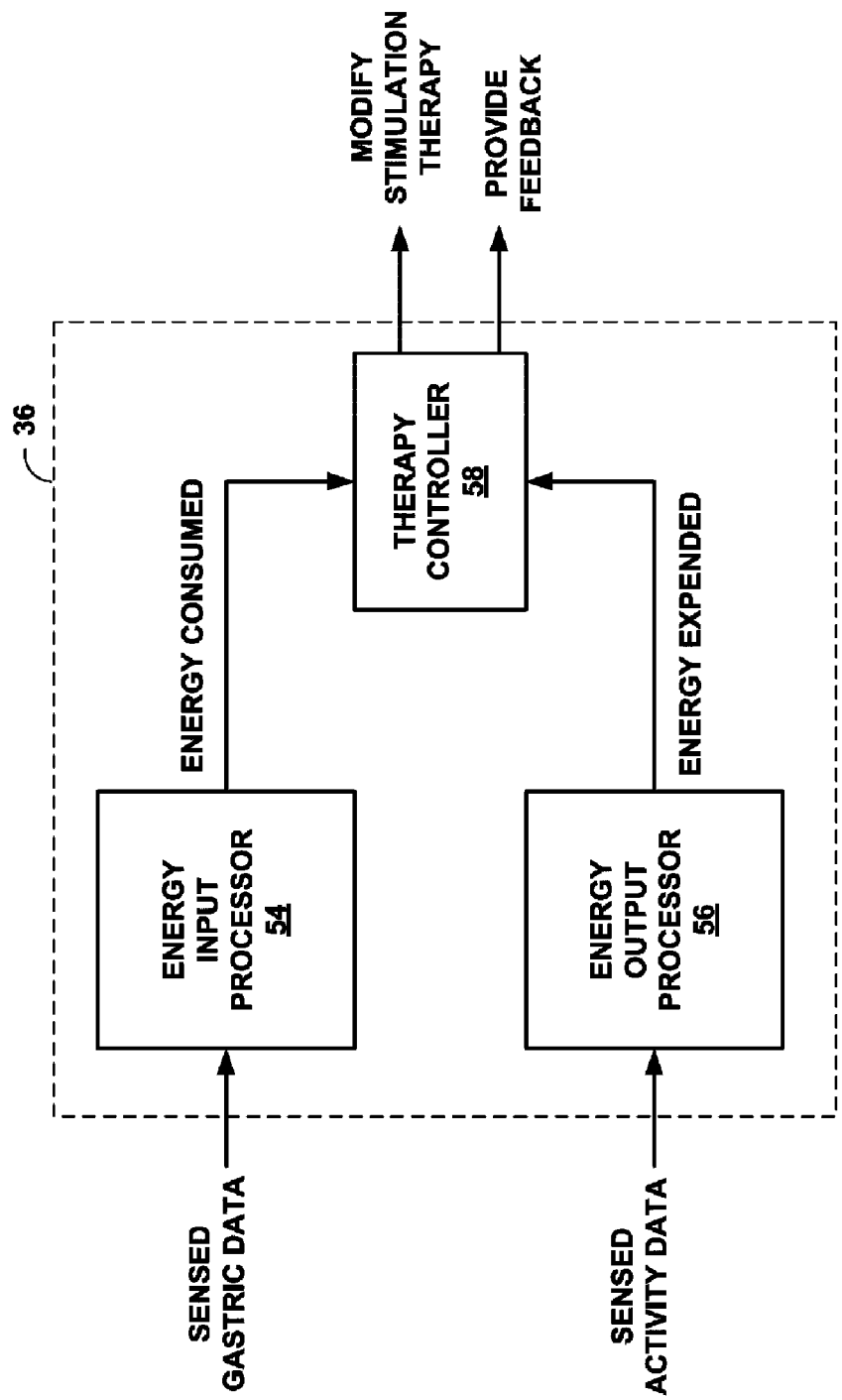
FIG. 3 is a block diagram illustrating functional components of a processor according to one exemplary embodiment of the invention.

FIG. 3 is a block diagram illustrating functional components of processor 36 according to one exemplary embodiment of the invention. Although described with respect to processor 36, in other embodiments, some or all of the illustrated functional components may be located externally to implantable stimulator 12, such as within external module 14 or within a central server with which external module 14 communicates via the Internet, a telephone line, or other telecommunications means. In the embodiment shown, processor 36 includes an energy input processor 54 and an energy output processor 56 that determine energy consumed and energy expended, respectively. Therapy controller 58 receives the determined values of energy consumed and expended and determines whether to provide feedback or modify stimulation therapy based on the received values. Again, energy input processor 54, energy output processor 56 and therapy controller 58 represent functional components of processor 36, and do not necessarily imply separate hardware, but rather programmable features.

Energy input processor 54 receives sensed gastric data from gastric sensor 30 (FIG. 2). Energy input processor 54 then processes and analyzes the sensed gastric data to obtain a value for energy consumed. For example, energy input processor 54 may determine a number of gastric contractions.

As described above, gastric sensor 30 may sense gastric electrical activity (GEA), and determine when contractions occur by noting when the gastric electrical activity is eliciting electrical response activity (ERA) that is morphologically different than fasted electrical control activity (ECA). Energy input processor 54 may detect ERA using band pass filtering to amplify spike activity, and may detect the spikes with a threshold comparator. The detection may be followed by a detection refractory period to avoid detection of the same ERA event. Energy input processor 54 may detect ERA using a wideband amplifier and analog or digital signal processing techniques to identify an event as an ERA event.

Alternatively or additionally, gastric sensor 30 may sense gastric contractions using a pressure sensor, a piezoelectric or triboelectric sensor, a strain gauge sensor, a gastric impedance sensor, an acoustic sensor, or an ultrasonic sensor. When using acoustic or ultrasonic sensors, gastric sensor 30 may use either single or dual sensor techniques. Energy input processor 54 may determine a number, force, or rate of gastric contractions based on the signals obtained by sensor 30. For example, a pressure excursion sensed by a pressure sensor or an electric charge excursion sensed by a piezoelectric or triboelectric sensor may represent a gastric contraction. Energy input processor 54 may use an energy input algorithm to estimate energy consumed based on the data relating to gastric contractions.

In some embodiments, energy input processor 54 may use fuzzy logic, neural networks, genetic algorithms, decision trees, or other types of algorithms for estimating energy consumed based on one or more types of gastric data. In one exemplary embodiment, energy input processor 54 may estimate energy consumed by multiplying the number of gastric contractions by a fixed number of calories per contraction. Using a fixed number of calories per contraction may be a good estimation of calories consumed because the amount of gastric juices released from the stomach and the volume of food moved into the intestine per contraction are related to the caloric density of the food in the stomach. For example, when patient 16 ingests food having high caloric density, the stomach will move a correspondingly reduced volume of the food into the intestine. Thus, each gastric contraction represents a relatively constant value of calories ingested. An average number of calories per contraction may be programmed into processor 36. The appropriate number of calories per contraction may be clinically calibrated for patient 16.

In one embodiment, processor 36 may continuously or periodically recalibrate the appropriate number of calories per contraction for patient 16 based on a physiological parameter, e.g., weight or body fat. For example, processor 36 may estimate a projected weight gain or loss based on the current stored number of calories per contraction. Processor 36 may compare an actual weight gain or loss of patient 16 to the projected weight gain or loss. Processor 36 may obtain the actual weight gain or loss based on manual entry of the patient's weight into external module 14. In some embodiments, the system may include a telemetry-enabled electronic scale that transmits the patient weight directly to processor 36 of implantable stimulator 12. If the actual and projected amounts are different, processor 36 may calculate the amount of calories per contraction associated with the actual weight gain/loss, and update the stored number of calories per contraction to reflect the most current value. A similar recalibration may be made based on a projected and actual amount of body fat of patient 16, where an impedance sensor on implantable stimulator 12 determines the actual amount of body fat by electrical impedance measurements.

Energy output processor 56 estimates a patient's energy expended based on sensed activity data. Energy output processor 56 may estimate a value of energy expended based on two components—basal metabolic rate and activity induced energy expenditure. Basal metabolic rate is energy expended in rest, and may be estimated based on age, sex, height and weight. Energy output processor 56 may be programmed with a value of basal metabolic rate for patient 16. Alternatively, energy output processor 56 may periodically or continuously estimate a basal metabolic rate based on the above factors along with body temperature, where activity sensor senses the body temperature of patient 16. In some cases, basal metabolic rate may be estimated for individual patients based on patient observation over a period of time.

Activity induced energy expenditure is energy expended in physical activity. Activity sensor 34 may be any of a number of sensors that can sense data that is used to calculate an amount of physical activity of patient 16. For example, a conventional activity sensor may include an accelerometer. However, in accordance with this disclosure, an activity sensor may also be a heart rate sensor, ECG sensor, minute ventilation sensor, or other type of sensor for sensing activity of patient 16. Activity data sensed by activity sensor 34 such as heart rate, heart rate variability, ECG, Q-T interval, night heart rate, cardiac variability index, minute volume, minute ventilation, blood oxygen level, blood pressure, body temperature, or activity are transmitted to energy output processor 56. Energy output processor 56 may use an energy output algorithm to estimate energy expended based on the sensed activity data. For example, energy output processor 56 may weight the various types of sensed activity data. In one embodiment, energy output processor 56 may use only one type of sensed activity data, such as accelerometer data. In some embodiments, energy output processor 56 may use fuzzy logic, neural networks, genetic algorithms, decision trees, or other types of algorithms for estimating energy expended based on one or more types of activity data, as well as cross-correlations among the data to provide a more accurate measure of patient activity level.

In addition, activity data may be used to monitor the condition of patient 16. For example, the ECG of patient 16 may be used to detect heart problems that may be caused or worsened by obesity of patient 16. Moreover, the activity data may be used to adjust the stimulation parameters for optimal neurological outcome that results in weight loss. For example, gastric stimulation parameters could be controlled by the degree of heart rate variability, the Q-T interval at specific heart rates, and the like.

Therapy controller 58 receives a value of energy consumed from energy input processor 54, and a value of energy expended from energy output processor 56. Therapy controller 58 may select either or both of energy input processor 54 and energy output processor 56 for receiving information. Therapy controller 58 may compare these values to stored goal values of energy consumed and energy expended. The goal values may indicate a cumulative amount of energy to be expended or consumed within a time period, such as a portion of a day, a day, a week, or other time period. For example, patient 16 may have a goal of expending 1000 calories by noon each day, and patient 16 may receive an alert if the goal is not met.

The goal values may be set by a physician, and may be set to change over time. For example, the goal energy expended may increase by a given percentage each day or week until reaching a fixed goal value. Similarly, the goal energy consumed may decrease until reaching a fixed goal value. The goal values may be tied to the patient's prior history of energy expenditure as measured by processor 36, such as a percent increase from a prior amount of energy expended by patient 16. The goal values may be stored in memory 38 and accessed by therapy controller 58. The goal values may be set and modified using external module 14 communicating with implantable stimulator 12, or by a physician responsible for programming the functionality of the implantable stimulator.

Therapy controller 58 may also calculate a value of net energy based on the energy consumed and energy expended. For example, therapy controller 58 may calculate net energy by subtracting the value of energy expended received from energy input processor 54 from the value of energy consumed from energy output processor 56. Therapy controller 58 may similarly compare the calculated net energy to a goal net energy amount. For an obese patient to lose weight, the patient must on average have a negative value of net energy. Therapy controller may make these comparisons and calculations continuously, periodically, or on demand. Therapy controller 58 may also calculate an amount of energy consumed or expended per unit time (e.g., per hour, per day, per week, or per month), and compare this to a goal amount of energy consumed or expended per unit time. This may allow for estimation of net energy within a given time frame.

In some embodiments, processor 36 may use a stored average value for one of the values of energy consumed and energy expended, and may calculate the net energy by comparing the stored average value to a value determined based on collected data. For example, instead of estimating the energy consumed based on sensed gastric data, energy input processor 54 may obtain an average value of daily energy consumed from memory 38. The average value of daily energy consumed may be calibrated for patient 16. Therapy controller 58 may then calculate daily net energy by subtracting a value of daily energy expended received from energy output processor 56 from the average daily energy consumed. As another example, instead of estimating the energy expended based on sensed activity data, energy output processor 56 may obtain an average value of daily energy expended from memory 38, which may be calibrated for patient 16. Therapy controller 58 may then calculate daily net energy based on the average daily energy expended and the energy consumed estimated by energy input processor 54.

Alternatively, data regarding one of the energy consumed and the energy expended may be obtained externally to implantable stimulator 12. For example, patient 16 may manually count daily calories consumed. In this case, patient 16 may enter the amount of calories consumed into external module 14, which in turn may communicate the amount to processor 36 via telemetry interface 40. Therapy controller 58 may then estimate net energy by subtracting the amount of energy expended, obtained from energy output processor 56, from the energy consumed received from external module 14. As another example, patient 16 may wear an external accelerometer as patient 16 conducts his daily routine. External module 14 may obtain accelerometer data from the external accelerometer and communicate the accelerometer data to processor 36 via telemetry interface 40. Processor 36 may estimate the patient's energy expended based on the received accelerometer data. Therapy controller 58 may then calculate net energy by subtracting the estimated amount of energy expended from the amount of energy consumed obtained from energy output processor 56.

Therapy controller 58 may select one or more actions to be taken based on comparisons of the determined energy consumed, energy expended, or net energy to goal values. For example, therapy controller 58 may alter stimulation therapy of patient 16 when the net energy of patient 16 is greater than a goal net energy. As another example, therapy controller 58 may activate alert module 50 to provide feedback to patient 16 in the form of an alert. Alert module 50 may provide an alert audibly or by vibration. Therapy controller 58 may trigger different types of alerts in different situations. Therapy controller 58 may use fuzzy logic, neural networks, genetic algorithms, decision trees, or other types of algorithms to select an action based on the energy values.

Therapy controller 58 may also communicate with external module 14 or other external device to provide other types of feedback to the patient or other user (e.g., a family member or doctor), such as by displaying graphics or text on a display. The feedback may indicate that patient 16 must take steps to adjust the energy balance, and may provide suggested actions. For example, a communication may indicate to patient 16 to stop eating, or to increase activity level. Alternatively or additionally, therapy controller 58 may cause external module 14 to display information relating to energy balance, such as net energy, energy consumed, or energy expended. For example, external module 14 may display a comparison of daily net energy with goal net energy in table or chart form. The data may be presented in a variety of ways, as discussed in further detail below. In some embodiments, external module 14, a central server, or a call center operator may select the appropriate actions to be taken in response to the energy determinations, and communicate the selection to therapy controller 58 via telemetry interface 40.

Figure 4:
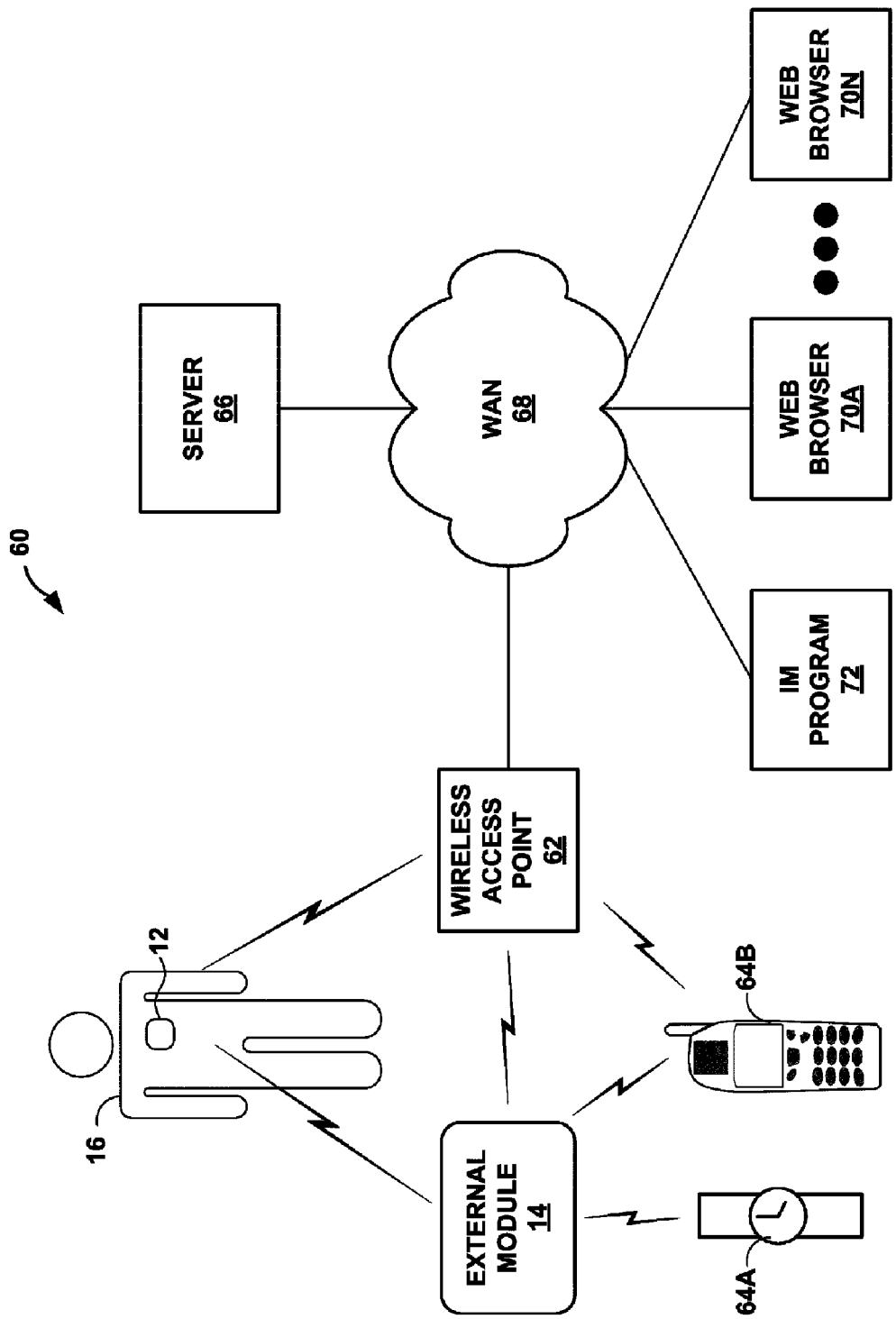
FIG. 4 is a block diagram illustrating an example system in which a patient receives obesity management feedback.

FIG. 4 is a block diagram illustrating an example system 60 in which a patient 16 receives obesity management feedback. System 60 includes patient 16 implanted with implantable stimulator 12. As shown in FIG. 4, implantable stimulator 12 communicates wirelessly with external module 14 via radio frequency (RF) telemetry, but the communication may also be transmitted via a wired connection, an optical connection, or a transcutaneous communication link. External module 14 may be a patient programmer, i.e., a device dedicated to receiving user input pertaining to electric stimulation and transmitting corresponding commands to implantable stimulator 12. Implantable stimulator 12 may be interrogated by, or may voluntarily transmit information to, external module 14. As discussed above, the information obtained from implantable stimulator 12 may be preprocessed by implantable stimulator 12, processed by external module 14, or both.

As shown, external module 14 may communicate with general purpose devices 64A, 64B. In the illustrated example, external module 14 communicates with general purpose devices including a wristwatch 64A and a cellular telephone 64B. In other examples, external module 14 may communicate with a pager, personal digital assistant (PDA), or other general purpose device (not shown), which may be carried by patient 16. General purpose devices 64 may display text or graphical indications to patient 16. In some embodiments, external module 14 may itself be a general purpose device such as a pager, cellular telephone, or PDA.

External module 14 may transfer information to a docking station (not shown) upon being placed in the docking station. In other embodiments, external module 14 may wirelessly transfer data to wireless access point (WAP) 62. Alternatively, implantable stimulator 12 may communicate directly with WAP 62. WAP 62 may communicate information to cellular telephone 64B. In some embodiments, WAP 62 may transfer information to a server 66 via wide area network (WAN) 68. Server 66 may be a central server of a patient management system, and WAN 68 may be the Internet.

Server 66 may present web pages containing information via web browsers 70A-70N ("web browsers 70") to users such as patient 16, or a doctor, family member, or caregiver of patient 16. Server 66 may also present information via an instant message (IM) program 72 to patient 16 or other user. Patient 16 may view the information presented by web browser 70A and IM program 72 on a home computer. For example, server 66 may cause patient 16 to receive an alert via wristwatch 64A, cellular telephone 64B, or IM program 72 that instructs patient 16 to stop consuming calories when patient 16 has consumed more calories than a goal amount of calories. As another example, patient 16 could receive an alert via wristwatch 64A, cellular telephone 64B, or IM program 72 to inform patient 16 that a preset amount of energy expenditure has not been achieved by a particular time or times each day.

In some embodiments, some or all of the illustrated functional components illustrated in FIG. 3 may be located externally to implantable stimulator 12, such as within external module 14 or within server 66. For example, processor 36 of implantable stimulator 12 may collect sensed gastric data and sensed activity data and communicate the collected data to external module 14 via telemetry interface 40. External module 14 may process and analyze the data, or may send the data to server 66 for processing and analysis. In another embodiment, processor 36 may provide some processing of the data, and external module 14 or server 66 may provide additional processing and analysis. For example, processor 36 may determine an estimated energy consumed and an estimated energy expended based on the sensed gastric data and sensed activity data, respectively, and provide this information to external module 14. External module 14 or server 66 may then determine an amount of net energy, and compare the estimated energy consumed, energy expended, and net energy to goal net energy.

Information may be presented to patient 16 and/or other users (e.g., a doctor, family member, or caregiver of patient 16) by any of external module 14, devices 64, web browsers 70 or IM program 72. The information may relate to the energy balance of patient 16, such as whether patient 16 has a positive or negative net energy value, or whether patient 16 is meeting goals for energy expended, energy consumed, and/or net energy. Information may be presented via visible or audible output media provided by external module 14, such as lights, LEDs, a display or an audio speaker. An audio message may take the form of an audible beep, ring, speech message or the like. The patient 16, physician, family members, or other caregivers may use the information to take action, such as making stimulation program changes, changing patient activity level, or changing patient food intake.

Figure 5:
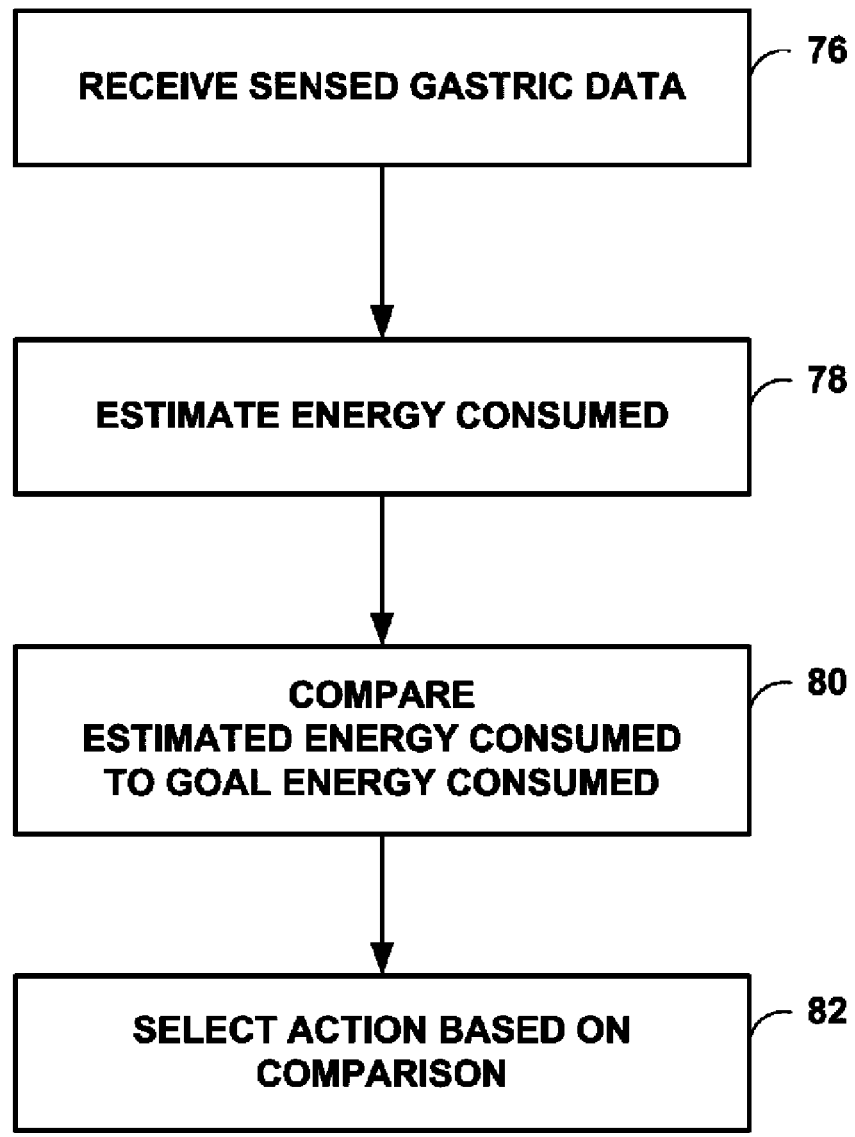
FIG. 5 is a flowchart illustrating an example mode of operation of processor in analyzing energy consumed.

FIG. 5 is a flowchart illustrating an example mode of operation of processor 36 in estimating and analyzing energy consumed. Processor 36 receives gastric data sensed by an implantable gastric sensor 30 (FIG. 2) (76). For example, sensed gastric data may include signals indicating gastric electrical activity (e.g, gastric slow wave), signals obtained by a pressure sensor, a piezoelectric or triboelectric sensor, a strain gauge sensor, a gastric impedance sensor, or an acoustic or ultrasonic sensor. Energy input processor 54 uses an energy input algorithm to estimate an amount of energy consumed based on the sensed gastric data (78). As described above, energy input processor 54 may estimate energy consumed by determining a number of gastric contractions based on the sensed gastric data, and multiplying the number of gastric contractions by a fixed number of calories per contraction.

Therapy controller 58 obtains the value of energy consumed from energy input processor 54 for analysis. For example, therapy controller 58 may compare the estimated energy consumed to a goal amount of consumed energy obtained from memory 38 (80). Therapy controller 58 may determine whether the estimated energy consumed is greater than the goal amount of energy consumed by a given amount or percentage of energy. Therapy controller 58 selects an appropriate action based on the comparison between the estimated energy consumed and the goal energy consumed (82). For example, therapy controller 58 may activate alert module 50 to issue an alert to patient 16. In one embodiment, therapy controller 58 may determine that patient 16 has consumed too many calories. The goal energy consumed may be associated with a time period, such as a maximum 600 calories in one forty-five minute time period.

If therapy controller 58 determines that patient 16 has exceeded the maximum amount of calories in the time period, therapy controller 58 may cause alert module 50 to alert patient 16 to stop eating. Hence, therapy controller 58 may deliver feedback as part of the patient's overall therapy and, in some embodiments, need not adjust electrical stimulation parameters. Alternatively or additionally, therapy controller 58 may modify stimulation therapy parameters in response to the comparison. Accordingly, therapy controller 58 may direct delivery of feedback, direct adjustment of stimulation therapy parameters, or direct delivery of feedback and adjustment of stimulation therapy parameters.

As one example, therapy controller 58 may increase stimulation when the patient's energy consumed is more than 5% greater than the goal amount of energy consumed. Therapy controller 58 may also provide feedback to patient 16 or another person, such as by a graphical display of the patient's energy consumed and goal energy consumed. Therapy controller 58 may also cause a list of suggested actions to be displayed to patient 16, such as to stop eating. Processor 36 may perform some or all of the above steps hourly, daily, on demand, or at other time interval as configured by a user.

Figure 6:
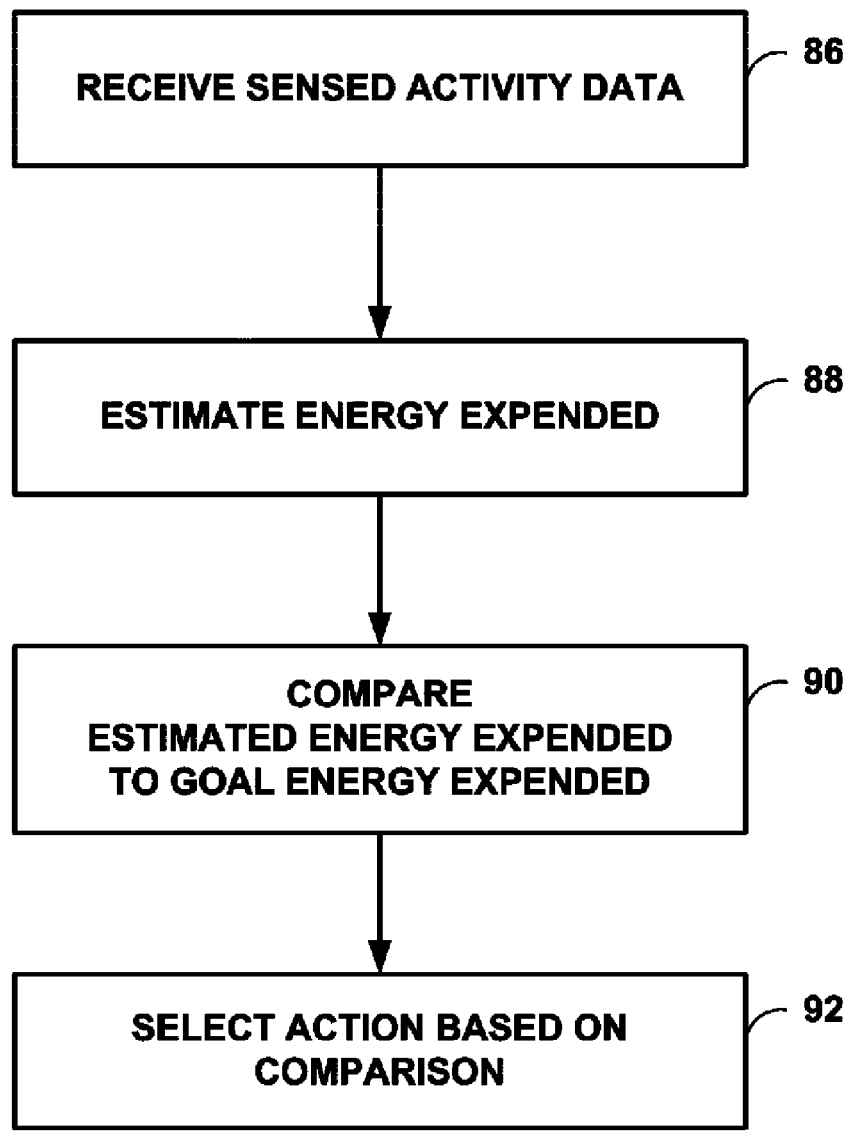
FIG. 6 is a flowchart illustrating an example mode of operation of processor in analyzing energy expended.

FIG. 6 is a flowchart illustrating an example mode of operation of processor 36 in estimating and analyzing energy expended. Processor 36 receives activity data sensed by activity sensor 34 (FIG. 2) (86). As described above, activity data may include signals indicating heart rate, heart rate variability, ECG, Q-T interval, night heart rate, cardiac variability index, minute volume, minute ventilation, blood oxygen level, blood pressure, body temperature, or activity. The above activity data may be obtained by any of a variety of conventional sensors. Energy output processor 56 uses an energy output algorithm to estimate an amount of energy expended based on the sensed activity data (88). In estimating the patient's energy expended, energy output processor 56 may use a fixed basal metabolic rate based on the patient's age, sex, height and weight, or may estimate a basal metabolic rate based on these factors and/or the patient's body temperature.

Therapy controller 58 obtains the value of energy expended from energy output processor 56 for analysis. For example, therapy controller 58 may compare the estimated energy expended to a goal amount of energy expended obtained from memory 38 (90). Therapy controller 58 may determine whether the estimated energy expended is less than the goal amount of energy expended by a given amount or percentage of energy. Therapy controller 58 selects an appropriate action based on the comparison between the estimated energy expended and the goal energy expended (92). For example, therapy controller 58 may activate alert module 50 to issue an alert to patient 16. As one example, therapy controller may cause alert module 50 within implantable stimulator 12 to vibrate when the patient's energy expended is below the goal amount of energy expended by 5% or greater. Therapy controller 58 may also provide feedback to patient 16 or another person, such as by a graphical display of patient's energy expended and goal energy expended. Processor 36 may perform some or all of the above steps hourly, daily, on demand, or at other time interval as configured by a user.

In one embodiment, processor 36 may receive activity data from an activity sensor that monitors an amount of time that patient 16 is active. For example, the activity sensor may be an accelerometer, and processor 36 may record and total a number of minutes patient 16 is active based on the data from the accelerometer. Processor 36 may provide an alert to patient 16 based on the data, such as by notifying patient 16 when patient 16 has not achieved a threshold number of minutes of activity in a given time period, such as a day or week. For example, processor 36 may notify patient 16 by activating an alert module 50 within implantable stimulator 12. Alert module 50 may, for example, notify patient 16 audibly or by vibration. For example, alert module 50 may take the form of a piezoelectric transducer that is energized in response to a signal from processor 36 in order to emit a sound or vibration. Alternatively, alert module 50 may apply electrical stimulation to the patient 16 at a level or in a pattern that is noticeable. This embodiment may be useful in teaching patient 16 to put in enough time exercising. In this embodiment, processor 36 may not calculate energy expended, but may simply take the activity data and provide feedback to patient 16 based on the activity data.

Figure 7:
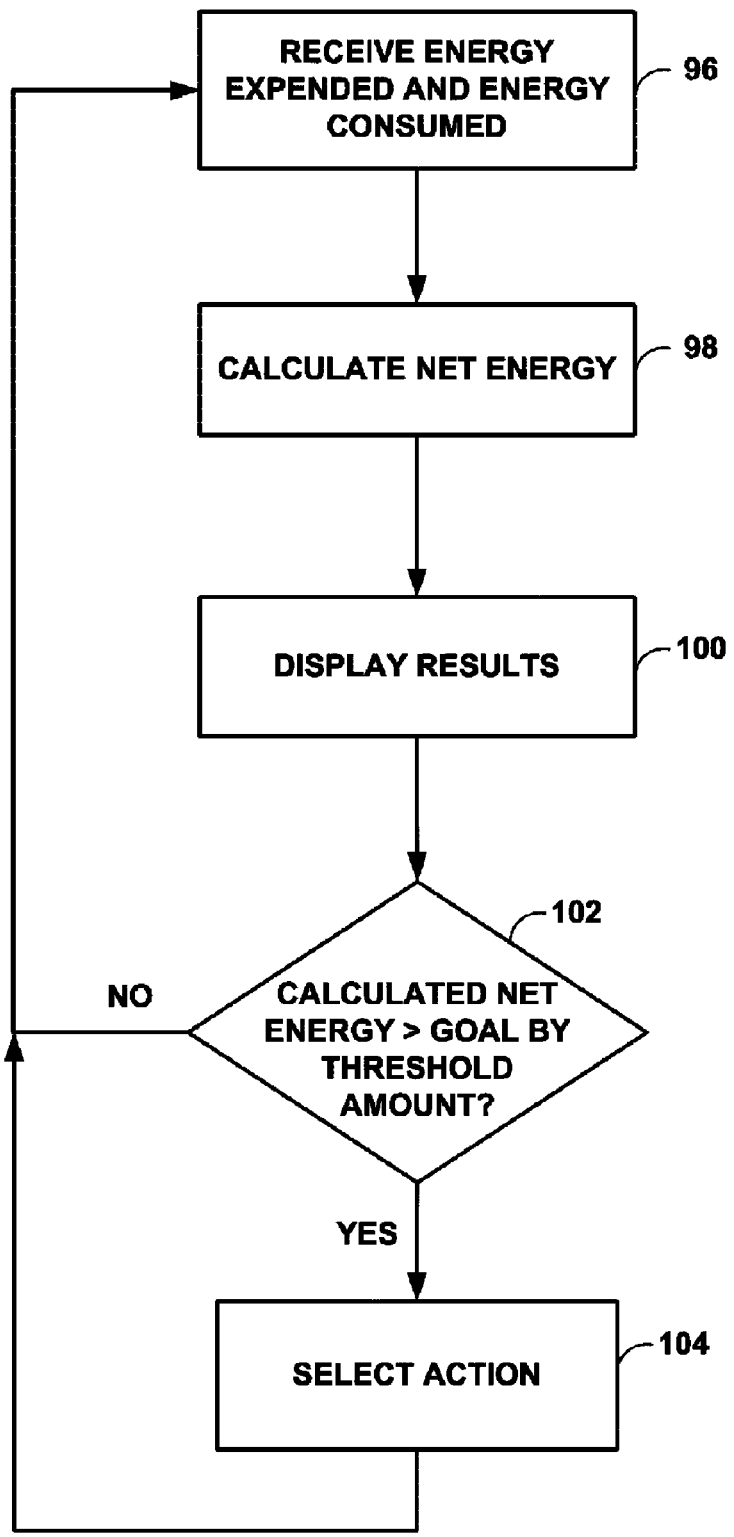
FIG. 7 is a flowchart illustrating an example mode of operation of a processor in analyzing net energy.

FIG. 7 is a flowchart illustrating an example mode of operation of processor 36 in analyzing net energy. Therapy controller 58 receives estimated amounts of energy consumed and energy expended from energy input processor 54 and energy output processor 56, respectively (96). Based on these estimated amounts of energy, therapy controller 58 calculates the patient's estimated net energy by subtracting the estimated energy expended from the estimated energy consumed (98). Therapy controller 58 may also compare the patient's estimated net energy to a goal net energy obtained from memory 38.

Therapy controller 58 may cause the results of the comparison to be displayed to the patient or to the patient's physician, family member, or caregiver (100). For example, therapy controller 58 may communicate information to external module 14 using telemetry interface 40. External module 14 or another external device may display the estimated net energy, energy consumed, and/or energy expended, and may display a comparison of these estimated values to corresponding goal values. Therapy controller 58 determines whether the calculated net energy is greater by the goal value by a threshold amount or percentage of energy (102). If so, therapy controller 58 may select an appropriate action to be taken in response to the determination, such as modifying the patient's stimulation therapy parameters, or providing feedback by providing information or invoking alert module 50 to provide an alert to patient 16 (104).

Figure 8:
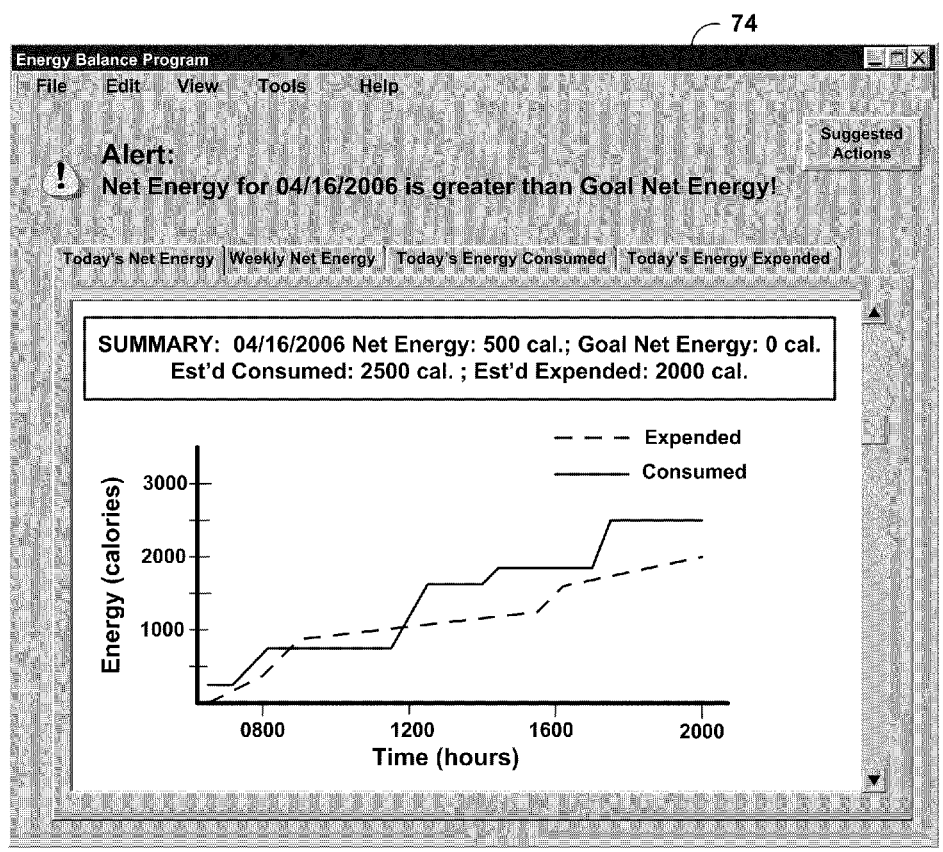
FIG. 8 is an exemplary screen illustration depicting an example energy balance report as viewed on a user interface.

FIG. 8 is an exemplary screen illustration depicting an example energy balance report 74 as viewed on a user interface. For example, energy balance report 74 may be viewed by patient 16 on web browser 70A of FIG. 4 or on a display associated with external module 14. In particular, energy balance report 74 represents a sample report entitled "Today's Net Energy." The report displays an alert that the actual net energy of patient 16 for a particular day is greater than the goal net energy. Energy balance report 74 further includes a summary of the amounts for net energy, goal net energy, estimated energy consumed, and estimated energy expended over the daytime hours of a single day. In the example of FIG. 8, patient 16 has consumed an estimated 2500 calories, and has expended an estimated 2000 calories, resulting in a net energy of 500 calories. The patient's actual net energy is greater than the goal net energy of zero calories.

Energy balance report 74 shows a graphical representation of the amount of energy consumed and expended over the day. This may assist the patient in understanding during which parts of the day he consumed and expended energy, and may help the patient in modifying his actions in the future to improve his energy balance. Energy balance report 74 includes a button labeled "Suggested Actions," which the user may click to view a list of suggested actions for patient 16 to take to improve his energy balance. The selected actions may include advice for increasing activity level, reducing food intake, or modifying stimulation therapy parameters.

The user may also click the tabs labeled "Weekly Net Energy," "Today's Energy Consumed," or "Today's Energy Expended" to view further information and graphical representations. The report of FIG. 8 is merely exemplary; other information may be presented, or other formats may be used. An energy balance program may present energy expended, energy consumed, or net energy over the course of a week, month, or other time period. The energy balance program may present trend information showing a trend of the total energy expended, energy consumed, or net energy over a time period so the user may track the patient's progress. The time period may be daily, weekly, monthly, or other time period.

The program may compare the patient's energy data for different time periods. In some embodiments, the data may be presented such that weekdays are only compared to other weekdays. The energy balance program may also present the goal amounts of energy expended, energy consumed, or net energy. For example, where the goal amounts are set to increase or decrease by a given amount or percent, the changing goal amounts may be shown to the user. The energy balance program may also present information to the user in the form of scorecards, tables, bar graphs, histograms, pie charts, or other types of representations.

The energy balance data may also be presented in conjunction with other data relating to the health or obesity management of patient 16, such as patient weight, blood pressure, and the like. This information may be displayed as a trend over a time period such as weekly, monthly, or longer.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure.

Various embodiments of the invention have been described. Although described with respect to an implantable stimulator, the principles of the invention may also be applied to gastric bands, vagal nerve stimulators, drug delivery systems, pacemakers, defibrillators, implantable glucose monitors, neurostimulators, pain control devices, or other implantable devices. Principles of the invention may also be applied to an implantable device implanted inside the stomach of a patient, such as a device placed in the stomach by an endoscopic procedure. In the example of a drug delivery system, the system may modify the drug dosage or rate based on the patient's overall energy balance as determined by the system. The term "drug delivery system" as used herein may include systems for delivery of drugs as well as systems for delivery of other substances, such as substances associated with protein therapy, e.g., hormones, polypeptides, proteins, enzymes, and the like. Moreover, although described as integrated into an implantable stimulator, the techniques described above may be applied to a dedicated implantable device that operates to provide feedback as described above. These and other embodiments are within the scope of the following claims.

The invention claimed is:

1. An implantable device comprising:
a sensor to sense gastric data; and
a processor operable to determine one or more characteristics of gastric contractions based on the sensed gastric data, estimate an amount of energy consumed by a patient based on the one or more characteristics of the gastric contractions, and control therapy to the patient based on the amount of energy consumed, wherein the one or more characteristics of the gastric contractions comprise at least one of a number of the gastric contractions, a force of the gastric contractions, and a rate of the gastric contractions.

2. The device of claim 1, wherein control of therapy by the processor includes directing delivery of feedback based on the amount of energy consumed.

3. The device of claim 1, wherein control of therapy by the processor includes modifying electrical stimulation parameters of an implantable stimulator implanted within the patient based on the estimated amount of energy consumed.

4. The device of claim 1, wherein control of therapy by the processor includes modifying drug therapy delivered by a drug delivery system implanted within the patient based on the estimated amount of energy consumed.

5. The device of claim 1, wherein the sensor is one of a gastric electrical activity sensor, a pressure sensor, a piezoelectric sensor, a triboelectric sensor, a strain gauge sensor, a gastric impedance sensor, an acoustic sensor, and an ultrasonic sensor.

6. The device of claim 1, wherein the one or more characteristics of the gastric contractions comprise a number of the gastric contractions, and wherein the processor estimates the amount of energy consumed by the patient based on the number of the gastric contractions.

7. The device of claim 6, wherein the processor estimates the amount of energy consumed by multiplying the number of the gastric contractions by an average amount of calories per contraction.

8. The device of claim 7, wherein the processor calculates a projected physiological parameter based on the average amount of calories per contraction, compares the projected physiological parameter to an actual physiological parameter, and recalibrates the average amount of calories per contraction based on the comparison, wherein the physiological parameter is one of patient weight and patient body fat.

9. The device of claim 1, wherein the processor compares the estimated amount of energy consumed to a goal amount of energy consumed, and provides feedback based on the comparison.

10. The device of claim 9, further comprising:
a telemetry interface,
wherein the processor provides feedback by transmitting a wireless communication to an external module via the telemetry interface.

11. The device of claim 1, wherein the one or more characteristics of the gastric contractions comprise the force of the gastric contractions, and wherein the processor estimates the amount of energy consumed by the patient based on the force of the gastric contractions.

12. The device of claim 1, further comprising at least one of an implantable stimulator and a drug delivery system, wherein control of therapy by the processor includes at least one of modifying electrical stimulation parameters of the implantable stimulator and modifying drug therapy delivered by the drug delivery system.

13. The device of claim 1, further comprising an activity sensor to sense activity data, wherein the processor is operable to estimate an amount of energy expended by the patient based on the sensed activity data.

14. The device of claim 13, wherein the activity sensor senses one of heart rate, heart rate variability, electrocardiogram (ECG), Q-T interval, night heart rate, cardiac variability index, minute volume, minute ventilation, blood oxygen level, activity level, blood pressure, and body temperature of the patient.

15. The device of claim 13, wherein the processor is operable to calculate an amount of net energy based on the estimated energy consumed and the estimated energy expended, compares the calculated net energy to a goal amount of net energy, and provides feedback based on the comparison.

16. The device of claim 13, wherein the processor is further operable to control the therapy based on the amount of energy consumed and the amount of energy expended.

17. The device of claim 1, wherein the one or more characteristics of the gastric contractions comprise the rate of the gastric constructions, and wherein the processor estimates the amount of energy consumed by the patient based on the rate of the gastric contractions.

18. An implantable device comprising:
a sensor to sense gastric data;
an activity sensor to sense activity data; and
a processor operable to estimate an amount of energy consumed by a patient based on the sensed gastric data and control therapy to the patient based on the amount of energy consumed, and operable to estimate an amount of energy expended by the patient based on the sensed activity data.

19. The device of claim 18, wherein the activity sensor senses one of heart rate, heart rate variability, electrocardiogram (ECG), Q-T interval, night heart rate, cardiac variability index, minute volume, minute ventilation, blood oxygen level, activity level, blood pressure, and body temperature of the patient.

20. The device of claim 18, wherein the processor calculates an amount of net energy based on the estimated energy consumed and the estimated energy expended, compares the calculated net energy to a goal amount of net energy, and provides feedback based on the comparison.

21. The device of claim 18, wherein the processor controls therapy based on both the amount of energy consumed and the amount of energy expended.

22. The device of claim 18, wherein control of therapy by the processor includes directing delivery of feedback based on both the amount of energy consumed and the amount of energy expended.

23. The device of claim 18, wherein control of therapy by the processor includes modifying electrical stimulation parameters of an implantable stimulator implanted within the patient based on both the amount of energy consumed and the amount of energy expended.

24. A system comprising:
an implantable device operable to sense gastric data, determine one or more characteristics of gastric contractions based on the sensed gastric data, and estimate an amount of energy consumed by a patient based on the one or more characteristics of the gastric contractions, wherein the one or more characteristics of the gastric contractions comprise at least one of a number of the gastric contractions, a force of the gastric contractions, and a rate of the gastric contractions; and
an external module, wherein the implantable device transmits a wireless communication to the external module to provide feedback based on the amount of energy consumed.

25. The system of claim 24, further comprising a network server, wherein the external module transmits information about the amount of energy consumed to the server and the server transmits the information to one or more network clients for viewing via a web browser, and wherein the web browser displays the information on a web page.

26. The system of claim 24, wherein the amount of energy consumed is displayed via one of the external module and the web page.

27. The system of claim 24, wherein the external module displays trend information about the amount of energy consumed during a time period.

28. The system of claim 24, wherein the external module is one of a patient monitor, a patient programmer, a physician programmer, a cellular telephone, a wristwatch, a personal digital assistant (PDA), and a pager.

29. The system of claim 24, wherein the one or more characteristics of the gastric contractions comprise a number of the gastric contractions, and wherein the implantable device estimates the amount of energy consumed by the patient based on the number of the gastric contractions.

30. The system of claim 24, wherein the implantable device senses activity data and estimates an amount of energy expended by the patient based on the sensed activity data.

31. The system of claim 30, wherein the implantable device is further operable to control therapy to the patient based on the amount of energy consumed and the amount of energy expended.

32. The system of claim 24, wherein the one or more characteristics of the gastric contractions comprise the force of the gastric contractions, and wherein the implantable device estimates the amount of energy consumed by the patient based on the force of the gastric contractions.

33. The system of claim 24, wherein the one or more characteristics of the gastric contractions comprise the rate of the gastric contractions, and wherein the implantable device estimates the amount of energy consumed by the patient based on the rate of the gastric contractions.

34. A system comprising:
an implantable device operable to sense gastric data and estimate an amount of energy consumed by a patient based on the sensed gastric data, and operable to sense activity data and estimate an amount of energy expended by the patient based on the sensed activity data; and an external module, wherein the implantable device transmits a wireless communication to the external module to provide feedback based on the amount of energy consumed.

35. The system of claim 34, wherein the implantable device calculates an amount of net energy based on the estimated energy consumed and the estimated energy expended, compares the calculated net energy to a goal amount of net energy, and provides feedback based on the comparison.

* * * * *

UNITED STATES PATENT AND TRADEMARK OFFICE
CERTIFICATE OF CORRECTION

| | |
|---|---|
| PATENT NO. | : 8,135,470 B2 |
| APPLICATION NO. | : 12/476893 |
| DATED | : March 13, 2012 |
| INVENTOR(S) | : John Keimel et al. |

It is certified that error appears in the above-identified patent and that said Letters Patent is hereby corrected as shown below:

Col. 19, Line 38:   ...gastric constructions...   Should Read As   ...gastric contractions...

Signed and Sealed this
Thirtieth Day of October, 2012

David J. Kappos
*Director of the United States Patent and Trademark Office*